United States Patent [19]

Satoh

[11] 4,234,404
[45] Nov. 18, 1980

[54] HORIZONTAL ELECTROPHORESIS OR ISOELECTRIC FOCUSING APPARATUS

[75] Inventor: Paul S. Satoh, Portage, Mich.

[73] Assignee: The Upjohn Company, Kalamazoo, Mich.

[21] Appl. No.: 29,063

[22] Filed: Apr. 11, 1979

[51] Int. Cl.³ .................. G01N 33/16; G01N 27/26
[52] U.S. Cl. .......................... 204/299 R; 204/180 R
[58] Field of Search ............ 204/180 R, 299 R, 301, 204/213

[56] References Cited

U.S. PATENT DOCUMENTS

| | | | |
|---|---|---|---|
| 2,249,609 | 7/1941 | Jackson | 204/213 |
| 2,566,308 | 9/1951 | Brewer | 204/299 R X |
| 2,632,730 | 3/1953 | Brannan | 204/213 X |
| 3,005,763 | 10/1961 | Kollsman | 204/213 X |
| 3,152,062 | 10/1964 | Clusius et al. | 204/301 |
| 3,330,753 | 7/1967 | Hepfer | 204/213 |
| 3,616,455 | 10/1971 | Von Münchhausen | 204/299 R |
| 3,616,456 | 10/1971 | Valmet | 204/299 R |
| 3,944,189 | 3/1976 | Singleton | 204/213 X |

Primary Examiner—Arthur C. Prescott
Attorney, Agent, or Firm—Blanchard, Flynn, Thiel, Boutell & Tanis

[57] ABSTRACT

Electrophoresis or isoelectric focusing of a starting species, in free solution, is performed in an elongated horizontal vessel, following which the vessel is turned about its horizontal longitudinal axis in order to move the separated fractions into separate collecting compartments contained within the vessel.

7 Claims, 10 Drawing Figures

HORIZONTAL ELECTROPHORESIS OR ISOELECTRIC FOCUSING APPARATUS

This invention relates to methods for performing horizontal electrophoresis or horizontal isoelectric focusing of starting species in free solution, in which the separated fractions are collected separately in compartments in the same vessel in which the electrophoresis or isoelectric focusing is performed, and an apparatus for use in performing those methods.

Electrophoresis and isoelectric focusing are well-known fractionation methods for separating molecules, bioparticles and macromolecules. In electrophoresis, particles or molecules having a net electric charge migrate electrophoretically, under the influence of an electric field, typically at a constant pH of, for example, about 8.6, at various rates depending on their electrophoretic mobility, toward the positive or negative electrode. In isoelectric focusing, amphoteric molecules and bioparticles, i.e., species capable of exhibiting positive, negative or zero electric charge as a function of pH, migrate electrophoretically, under the influence of an electric field and a pH gradient, until they are condensed or focused at positions that correspond to their respective isoelectric points whereat their net charge approaches zero. Although the principles of fractionation are different in the two methods, the two methods are closely related fractionation methods and similar procedures and apparatus can be used in the two methods. A principal operational difference in the two methods is that in isoelectric focusing a carrier ampholyte liquid is used, whereas in electrophoresis an electrically conductive electrophoresis medium is used.

This invention is useful for both electrophoresis and isoelectric focusing. For purposes of simplifying the following description, the term "electrophoresis" will be principally used in the following description, but it will be understood that the term refers to both electrophoresis and isoelectric focusing, unless the context specifically requires otherwise.

Further, in the following description, the term "starting species" means the starting material that is to be subjected to electrophoresis in order to effect separation of the components thereof. For example, the starting species can be a mixture of lymphocytes or a mixture of serum proteins which is to be subjected to electrophoresis in order to resolve same into fractions of more closely homogeneous characteristics. Moreover, the term "free solution" refers to the fact that the starting species is carried in a liquid carrier medium so as to be freely movable therein. The starting species can be dissolved or suspended in the liquid carrier.

A wide variety of satisfactory preparative electrophoresis methods and apparatus are known in the art. However, the prior art apparatuses which are useful for obtaining a large number of separate fractions of the starting species are quite complex and expensive, and the methods of using them are time-consuming and technically involved. There is a need for a simpler, less expensive and easier-to-use electrophoresis method and apparatus for separating a starting species into a large number of fractions and recovering those fractions.

It is an object of this invention to provide an improved electrophoresis method and apparatus in which the starting species is placed in an elongated horizontal vessel and then is subjected to electrophoresis therein to separate the starting species into fractions which are displaced horizontally along the lengthwise extent of the horizontal vessel, following which the vessel is turned about its horizontal longitudinal axis so that the separate fractions are moved into and are separately collected in different manually isolated compartments in the vessel whereby the fractions can be recovered separately from one another with minimal cross-contamination of the fractions.

It is a further object of this invention to provide an improved electrophoresis method and apparatus which can be used to separate human peripheral blood lymphocytes by electrophoresis.

It is a further object of this invention to provide an improved method and apparatus, as aforesaid, in which amphoteric macromolecules or cells can be separated into fractions by isoelectric focusing.

It is another object of this invention to provide an improved method and apparatus, as aforesaid, in which the starting species, in free solution, migrate electrophoretically in a horizontal direction in the vessel, under the influence of an electric field and under conditions which minimize the risk of damage to components of the starting species.

It is a further object of this invention to provide an improved method and apparatus, as aforesaid, which is simple and easy to use, which is rapid in operation, and which does not require the use of a density gradient material or separate collecting vessels for receiving the separated fractions.

Additional objects and advantages of the invention will become apparent upon reading of the following detailed description and inspection of the accompanying drawings.

Figure 1:
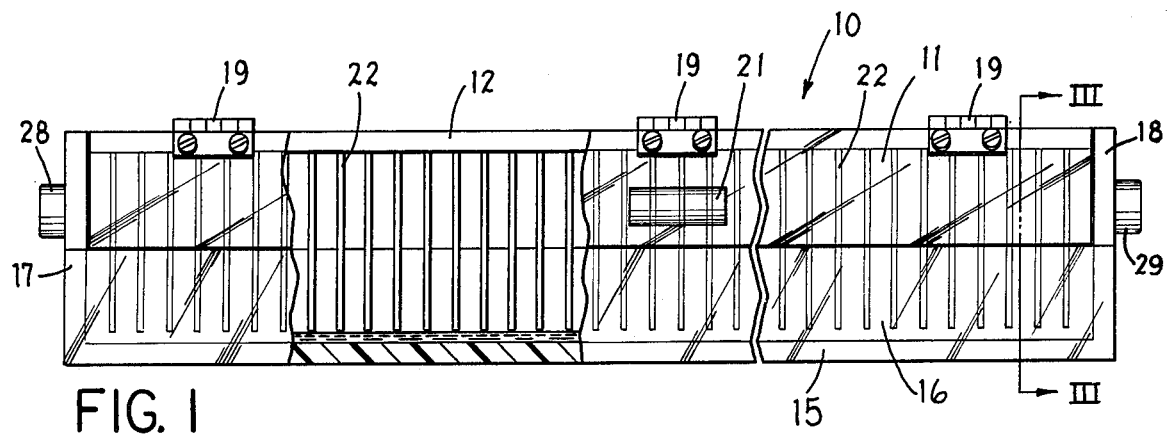
FIG. 1 is a front view, partially broken away, of a horizontal electrophoresis vessel according to the invention.
Figure 2:
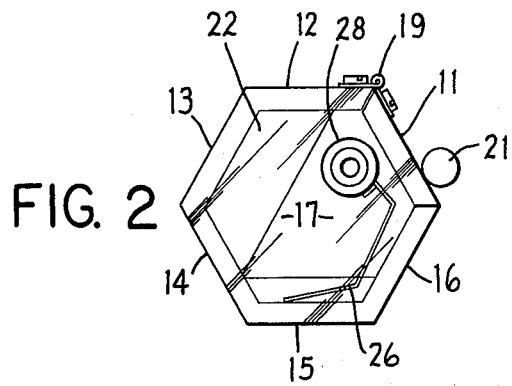
FIG. 2 is an end view of the electrophoresis vessel of FIG. 1.

According to the invention, there is provided a hollow, elongated, horizontal, electrophoresis vessel which has electrophoresis electrodes therein adjacent the opposite ends thereof. An unobstructed zone is provided in the interior of the electrophoresis vessel. The unobstructed zone is located at the bottom of the vessel when the vessel is positioned in its normal position for electrophoresis. There also is provided a multiplicity of upright, generally parallel, horizontally spaced-apart partitions within the vessel defining a multiplicity of separate, isolated compartments which are located above the unobstructed zone in which the electrophoresis is carried out.

In the method according to the invention, a quantity of the starting species carried in a liquid electrophoresis medium is deposited into the unobstructed zone along the bottom of the electrophoresis vessel so as to form a liquid layer therein. This liquid layer remains substantially stationary during the electrophoresis operation. Further, the liquid layer is in contact with the electrophoresis electrodes. An electrophoresis potential difference is applied across the electrodes whereby to cause the components of the starting species to migrate electrophoretically in a horizontal direction in the layer whereby the starting species becomes separated into fractions which are horizontally displaced from one another in a direction lengthwise of the vessel, owing to their different electrophoretic mobilities when electrophoresis is being carried out, or owing to their different isoelectric points when isoelectric focusing is being carried out. After completion of the electrophoresis operation, application of the electrophoresis potential is discontinued, and then the vessel is turned through an arc about its horizontal longitudinal axis so as to position the partitions lowermost whereby to cause the liquid layer to flow into the compartments in the electrophoresis vessel. Thereby, the respective fractions are separately achieved in separate isolated compartments in the electrophoresis vessel. The separated functions can then be individually removed from the respective compartments and placed in different containers for further purification and/or analysis. Thus, from the starting species, there are recovered a multitude of different fractions containing different components of the starting species and wherein the respective fractions are more closely homogeneous than the starting species.

It is preferred that the unobstructed zone in the electrophoresis vessel contains a lower substrate layer of liquid or solid, flowable material which is inert in the electrophoresis operation and which rests on the bottom of the vessel. The layer of the starting species and electrophoresis carrier medium is deposited on the substrate layer, whereby to form an upper layer lying on top of the substrate layer. In this way, the starting species, in effect, floats above the substrate layer whereby to reduce sliding friction effects. It is preferred to use a lower substrate layer which is a liquid, such as sucrose solution, in order to minimize friction. However, it is also within the scope of the broader aspects of the present invention to use a lower substrate layer which is a granulated gel of Sephadex (Trademark) or Bio-Gel (Trademark) material, both of which are well-known materials used in the electrophoresis art.

The use of a lower flowable substrate layer of inert material is highly advantageous when the starting species is comprised of substances which are sensitive to sliding friction, such as live cells. For example, if a layer containing a starting species comprised of lymphocytes were to be placed directly on the bottom of the electrophoresis vessel, damage to the lymphocytes could occur because of the movement of the lymphoctyes along and in contact with the bottom wall. In contrast, when the starting species is placed as an upper layer on top of a lower flowable substrate layer, as described above, the starting species does not directly contact the bottom wall of the electrophoresis vessel and there is a much reduced opportunity for the occurrence of damage to the starting species.

Thus, the preferred embodiment of the present invention provides a two-phase electrophoresis system wherein the starting species is present in the upper phase of that system. That two-phase system can be a solution-solution system when the lower substrate layer is a liquid or it can be a solution-flowable solid system when the lower phase comprises gel particles. Not only in the opportunity for damage to the starting species reduced, but also the speed of separation of the fractions is improved by this two-phase technique. It is to be noted, moreover, that the method of the present invention does not involve the creation of a density gradient within the upper layer, but rather, the electrophoresis is carried out with the starting species dissolved or suspended in a liquid carrier medium.

In carrying out a strictly electrophoresis separation under a substantially constant pH, the liquid electrophoresis carrier medium is an electrically conductive liquid. Further, when the starting species comprises living things, such as lymphocytes, the electrophoresis medium is also isotonic. On the other hand, when the starting species comprises non-living things, the electrophoresis carrier medium need be only electrically conductive.

Further, with reference to strictly isoelectric focusing, the electrophoresis medium comprises a carrier ampholyte liquid, such as Ampholine (trademark) liquids, which are commonly used in isoelectric focusing.

Suitable liquid mediums for electrophoresis separations and isoelectric focusing separations are well known to workers skilled in the art. Applicant's invention does not pertain to any discovery relating to such mediums.

Referring to FIGS. 1 through 6 of the drawings, there is shown a horizontal electrophoresis vessel which is useful for carrying out the methods described above. The horizontal electrophoresis vessel is a hollow, hexagonal, elongated housing 10 defined by six side wall portions 11, 12, 13, 14, 15 and 16 which are arranged to define a hollow hexagonal tube. The opposite ends of the hexagonal tube are closed by two hexagonal end walls 17 and 18. The side wall portion 11 is hingedly connected along one longitudinal edge thereof to the adjacent side wall portion 12 by hinges 19. The side wall portion 11 has a handle 21 attached thereto so that the side wall portion 11 can be moved between open and closed positions for access to the interior of the housing 10.

The housing 10 is made of electrically insulating material. It is preferred that one or more of the wall portions 11–16 and the end walls 17 and 18 are transparent to permit visual inspection of the contents of the housing 10 during the electrophoresis operation. In the illustrated preferred embodiment of the invention, all of the wall portions 11–16 and the end walls 17 and 18 are made of a transparent synthetic resin which is suitable for use with the materials and under the conditions employed in electrophoresis operations. Moldable, transparent, acrylic resins, such as polymethyl methacrylate, are highly satisfactory synthetic resins for this purpose.

Figure 3:
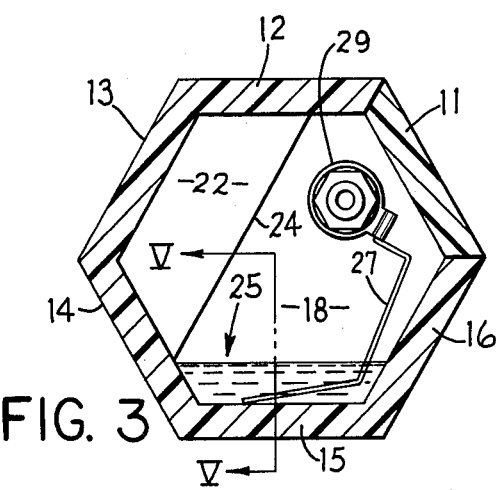
FIG. 3 is a sectional view, taken along the line III—III of FIG. 1, showing the cross section of the electrophoresis vessel, shown in the normal position thereof while the electrophoresis operation is being carried out.

A plurality of upright, parallel, horizontally spaced-apart partitions 22 are mounted inside the housing 10. The partitions 22 are planar, trapezoidal plates which extend in planes perpendicular to the horizontal longitudinal axis of the housing 10. The partitions extend from one side wall portion 12 along the side wall portion 13 to the side wall portion 14 of the housing. The side edges and outer edge of the partitions 22 are united to the inner surfaces of the side wall portions 12, 13 and 14, whereby the partitions divide the zone between the side wall portions 12, 13 and 14 into separate comparatments 23 which are isolated from each other. The partitions 22 occupy less than one-half of the total cross-sectional area of the interior of the housing 10 and the inner edges 24 of the partitions are laterally outwardly spaced from the juncture of wall portions 11 and 12 and from the juncture of wall portions 14 and 15. The space above the wall portion 15 up to the inner edges 24 of the partitions defines an unobstructed zone 25 in which the electrophoresis is performed. Thus, when the starting species and the electrophoresis liquid is placed in the housing 10 so as to form a layer on the bottom wall portion 15 thereof, as shown in FIG. 3, the level of the upper surface of the sample species is not higher than the lower end of the compartments 23, whereby the components of the starting species are capable of free lengthwise horizontal flow in the housing during the electrophoresis operation without hindrance from the partitions 22.

The partitions 22 are made of electrical insulating material and, advantageously, they are made of the same synthetic resin as the housing 10.

It will be appreciated that the housing 10 can be built up, for example, by adhesively securing together wall sections 11–16 together along their adjacent edges. For example, the wall sections 12, 13 and 14 can be assembled to each other, the partitions 22 can then be mounted therein, following which the remaining wall sections 15, 16 and 11 can be attached thereto in order to complete the formation of the housing 10 having the partitions 22 therein. The end walls 17 and 18 can be similarly secured to the ends of the wall sections 12–16.

Electrodes 26 and 27 suitable for electrophoresis purposes are mounted on the end walls 17 and 18, respectively. The electrodes 26 and 27 are wire-like conductors made, for example, of platinum, and they are located close to and they extend substantially parallel to the interior surfaces of the end walls 17 and 18. The electrodes have lower legs which extend into zone 25 and close to the wall portion 15 so that they contact the electrophoresis liquid during the electrophoresis operation. The shapes of the electrodes 25 and 26 are not critical and they are here shown as conforming roughly to the shape of the housing 10.

Electrical connectors 28 and 29 are mounted on the end walls 17 and 18 at any suitable locations thereon. Here the connectors 28 and 29 are positioned close to the juncture of the wall portions 11 and 12 and laterally spaced from the inner edges 24 of the partitions 22. The electrodes 26 and 27 are connected to the connectors 28 and 29. The connectors 28 and 29 are adapted to be connected to the terminals of any suitable electrophoresis power source so that one of the electrodes serves as the cathode and the other of the electrodes serves as the anode during electrophoresis.

Figure 4:
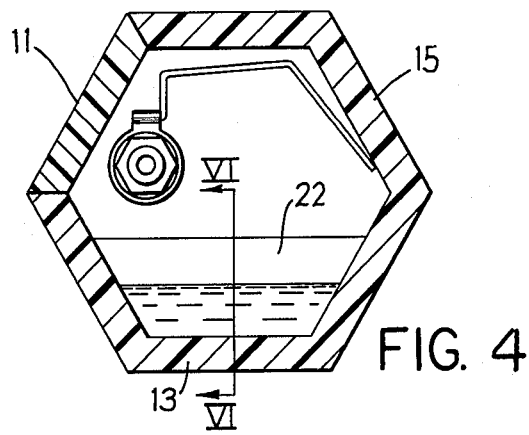
FIG. 4 is a view similar to FIG. 3, but in which the electrophoresis vessel has been turned through an arc of about 120° about its horizontal longitudinal axis, after completion of the electrophoresis operation, so that the separated fractions are received in the compartments in the vessel.
Figure 5:
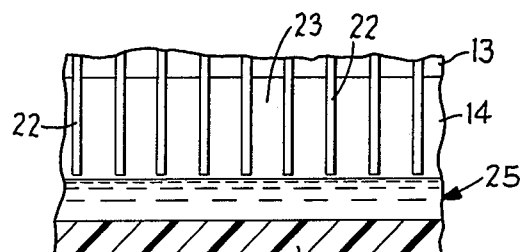
FIG. 5 is a sectional view taken along the line V—V of FIG. 3.
Figure 6:
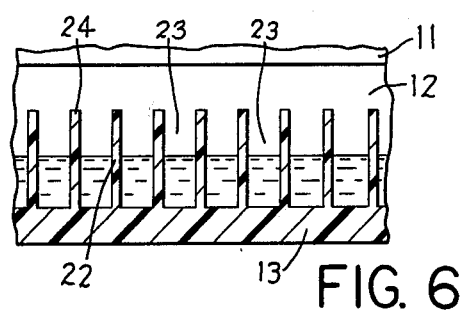
FIG. 6 is a sectional view taken along the line VI—VI of FIG. 4.

The apparatus can be used to perform either electrophoresis or isoelectric focusing of the starting species in free solution. In both methods, the housing 10 is positioned horizontally with the wall portion 15 being located lowermost so that the electrophoresis liquid rests on the wall portion 15, as shown in FIG. 3. The electrophoresis potential source connected to the electrodes 26 and 27 applies an appropriate electrophoresis potential and current for the appropriate period of time effective to separate the starting species into fractions. During such electrophoresis, the electrophoresis liquid, as a whole, remains stationary on the wall portion 15 when the apparatus is placed on a level horizontal surface, but the different molecules or bioparticles of the sample species will migrate in a lengthwise direction in the housing different horizontal distances because of electrophoretic effects so that the starting species becomes separated into fractions which are horizontally displaced and are laterally aligned with different ones of the compartments 23 or at least different groups of adjacent compartments. When electrophoresis is completed, the electrophoresis potential source is turned off. The housing 10 is then carefully turned about its horizontal longitudinal axis so as to rest on wall 14 and then on wall 13, as shown in FIG. 4. The liquid thereby enters into the respective compartments 23 whereby the liquid becomes subdivided into separate electrophoresed fractions. This turning operation is carried out as carefully as possible so as to minimize cross-contamination of the fractions due to unwanted mixing of horizontally adjacent fractions. The thus-separated fractions can be removed from the respective compartments and placed in separate receptacles, such as test tubes, for the purposes of further separation and/or analysis.

The movable wall section 11 makes it possible to insert the electrophoresis liquid into the vessel 10 and also to remove the separated fractions from the vessel. During the electrophoresis operation, the wall section 11 will be in the closed position in order to prevent contamination of the contents of the vessel.

The location of the position at which the starting species is placed in the vessel 10 prior to starting electrophoresis is not critical. Because it is desired to carry out the separation as rapidly as possible, the operator will normally place the starting species at a position, in the lengthwise direction of the vessel 10, at which he expects the separation to be completed most rapidly without cross-contamination of the fractions. This will depend on the specific components of the starting species, that is, whether they have a net positive or a net negative charge in the case of electrophoresis, or the character of their isoelectric points in the case of isoelectric focusing. Normally, the operator will have had some experience which will lead him to believe that inserting the starting species at a particular location will give the best results. However, even if the place of insertion of the starting species is not the optimum location, still the electrophoresis separation can be achieved, although possibly a longer time will be required. In the case of a starting species whose characteristics are not known, it will normally be placed at approximately the longitudinal midpoint of the housing 10.

The number of compartments 23 in the vessel 10 can be selected to meet the requirements of the particular separation desired to be effected therein. Although the number of compartments is not critical, it is generally useful in electrophoresis separations to use vessels containing from 10 to about 50 compartments.

MODIFICATION

Figure 7:
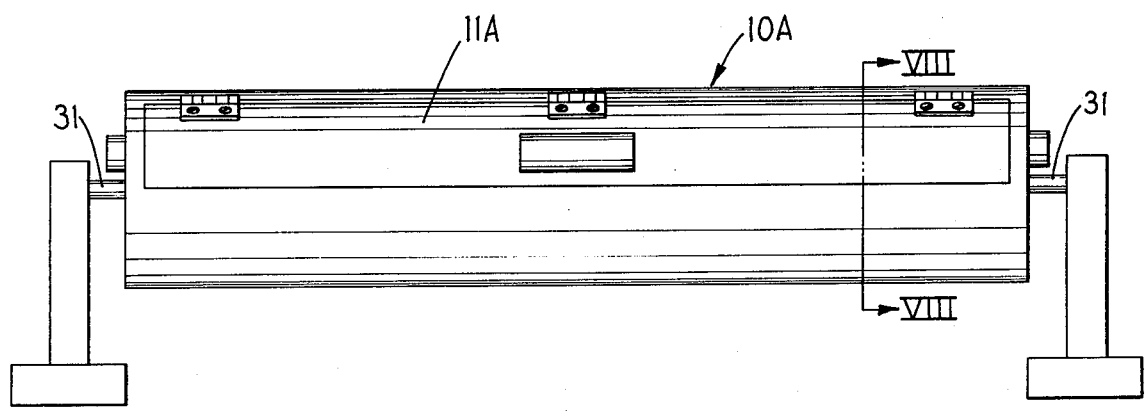
FIG. 7 is a schematic view of a modified horizontal vessel according to the invention.
Figure 8:
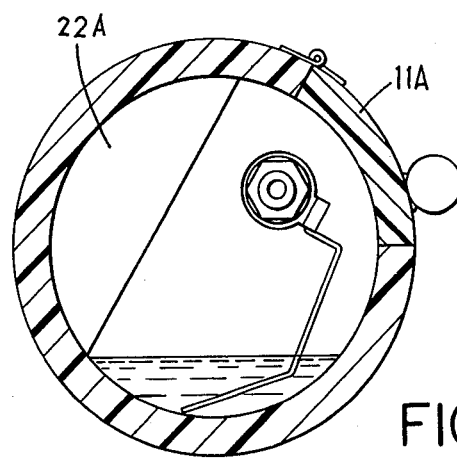
FIG. 8 is a sectional view taken along the line VIII—VIII of FIG. 7.

Referring to FIGS. 7 and 8, there is illustrated a modified electrophoresis vessel 10A which is supported for rotation by the axles 31. The modified electrophoresis vessel is of circular cross section. The electrophoresis vessel 10A has a door section 11A to provide access to the interior of the vessel and it also has a series of partitions 22A disposed above the bottom portion of the vessel to provide compartments, like the compartments described above with respect to the principal embodiment of the invention. As shown, the partitions are in the form of segments of a circle and they occupy a relatively large proportion of the cross-sectional area of the central circular opening in the housing 10A. The method of operation of the modified embodiment of the invention will be the same as described above with respect to FIGS. 1 through 6.

EXAMPLE 1

Figure 9:
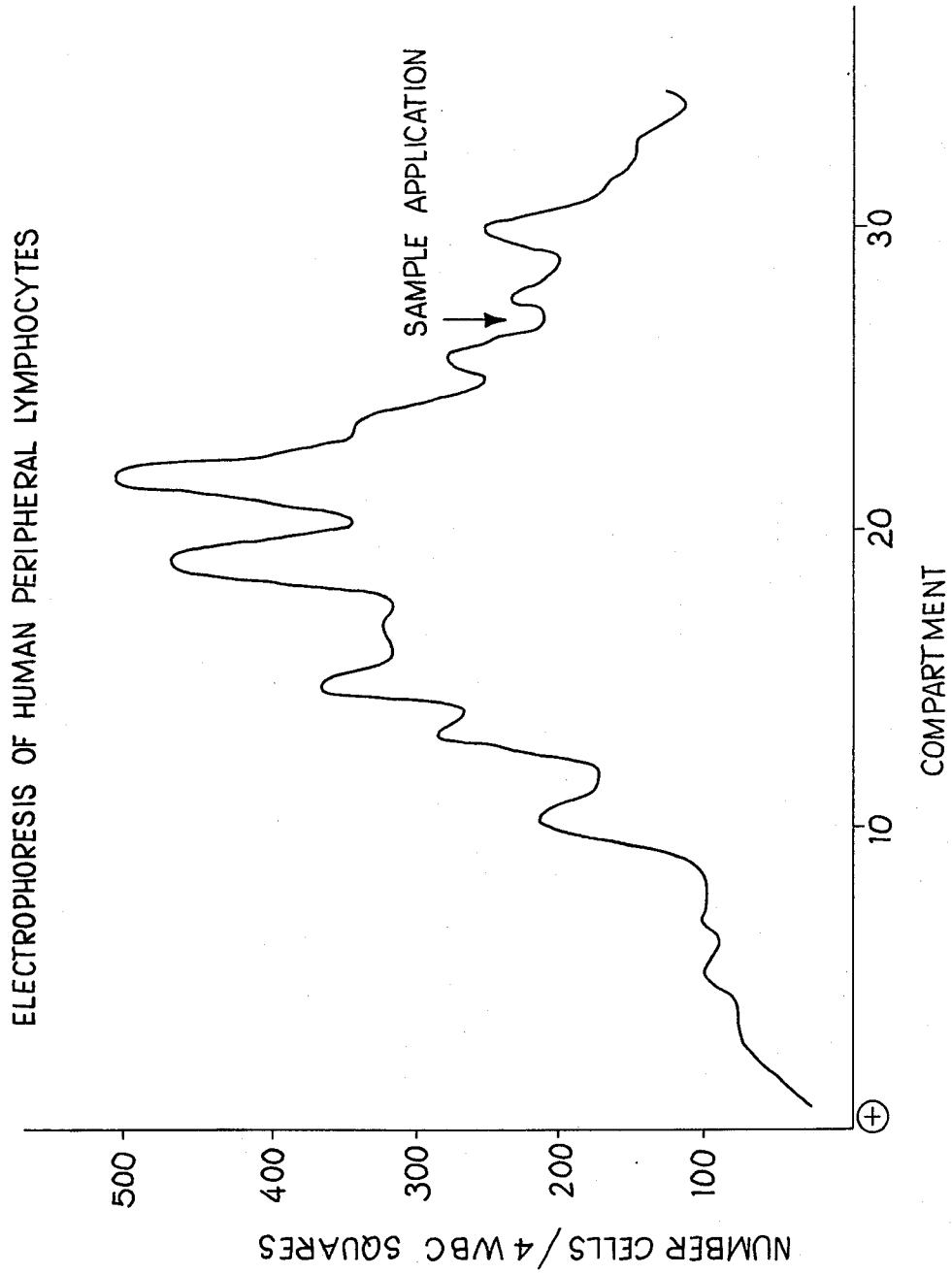
FIG. 9 is a graph showing the results of a typical electrophoresis method according to the invention.

Heparinized venous blood was diluted twice with phosphate buffered saline (PBS) at pH 7.4 and was layered over Ficoll-Hypaque (Lymphoprep, Nyegaard Scientific) solution and centrifuged at 400×g for 20 minutes to obtain a lymphocyte-rich suspension. The suspension of the lymphocytes was washed once with PBS and the concentration of the cells was adjusted to approximately $10^9$ per ml. Then, $1 \times 10^8$ of the thus-isolated lymphocytes in 2 ml of Hank's balanced salt solution were carefully placed on a layer of 25 ml of Ficoll-Hypaque solution in the midsection of the electrophoresis vessel 10. In this position, the position of the vessel 10 was as shown in FIG. 3. The lymphocytes were subjected to electrophoresis at 30 V, 25 ma for 3 hours, at room temperature. Electrophoresis was discontinued and then the vessel 10 was turned from the FIG. 3 to the FIG. 4 position, i.e., a counterclockwise turning through an arc of 120° whereby the separated fractions were collected in the compartments. A reasonable separation of cell sub-populations was obtained, as shown in FIG. 9. The average viability of the separated cells was greater than 80%.

EXAMPLE 2

Figure 10:
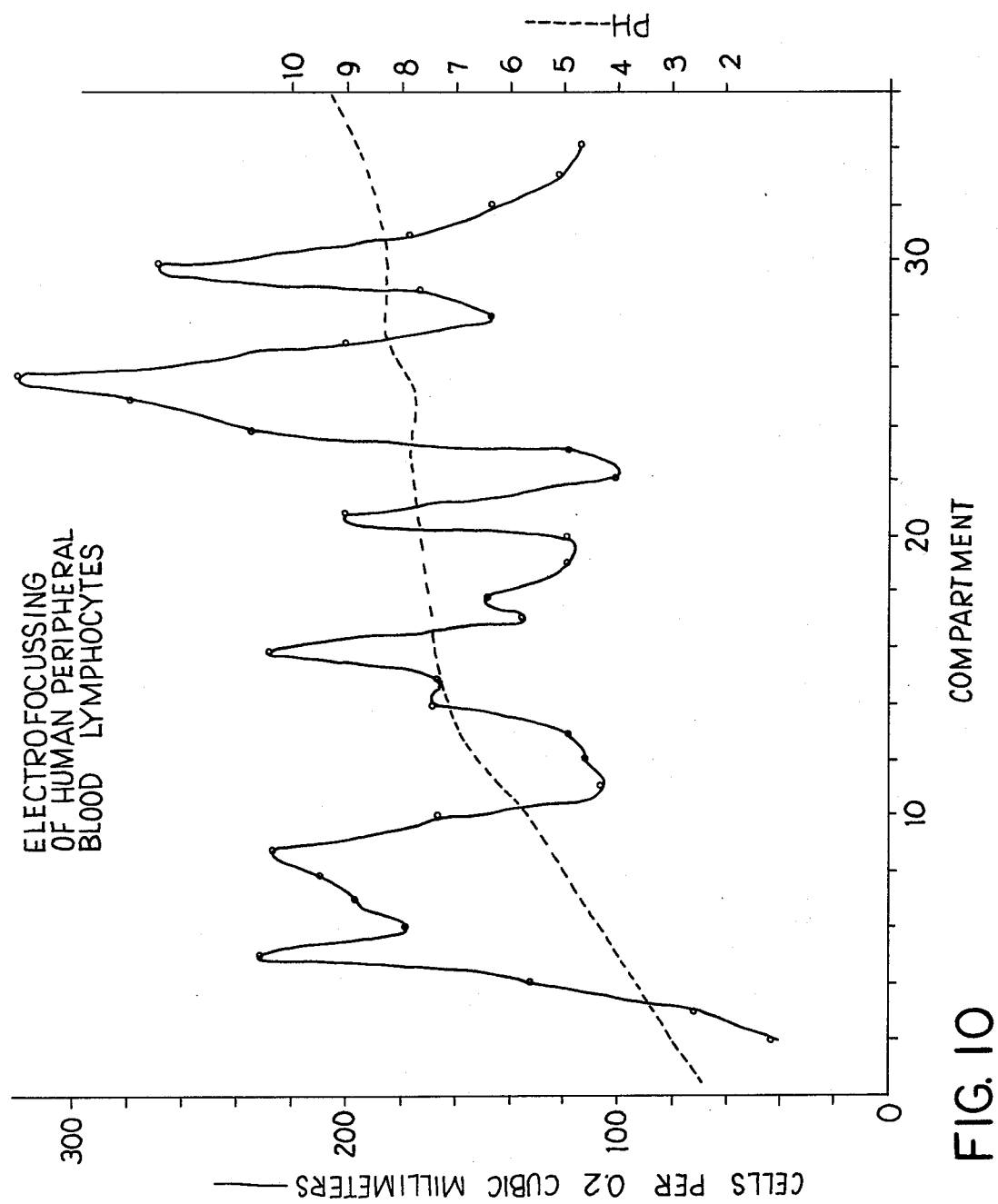
FIG. 10 is a graph showing the results of a typical isoelectric focusing method according to the invention.

For electrofocusing of cells, 25 ml of Lymphoprep was mixed with 2 ml of Ampholine (Trademark) (pH 5-7) over which $10^8$ lymphocytes in 0.2 ml Hank's balanced salt solution were applied at the midsection of the electrophoresis vessel positioned as shown in FIG. 3. The mixture of cells and Lymphoprep was electrofocused at 25 V D.C. 20-25 ma for 4 hours at room temperature. At the end of the electrophoresis, the vessel was rotated to the FIG. 4 position in order to collect the separated fractions. Each fraction was then transferred to a test tube and was centrifuged. The results of this electrofocusing operation are shown in FIG. 10.

Although particular preferred embodiments of the invention have been described above, the invention contemplates such changes or modifications as lie within the scope of the appended claims.

The embodiments of the invention in which an exclusive property or privilege is claimed are defined as follows:

1. An electrophoresis or isoelectric focusing apparatus comprising:
   an elongated, electrically non-conductive, horizontal vessel having wall means defining an impermeable side wall and a pair of impermeable end walls; a pair of horizontally spaced-apart electrodes disposed inside said vessel close to the opposite ends thereof and adapted to be connected to a source of electrical potential for electrophoresis or isoelectric focusing; said vessel having therein a multiplicity of electrically non-conductive, impermeable, upright, generally parallel, horizontally spaced-apart partitions extending from one portion of said side wall transversely to the longitudinal axis of said vessel and partway across the cross section of said vessel, said partitions terminating at locations transversely spaced from the portion of said side wall that is opposed to said one portion of said side wall, so as to divide the space within said vessel into an unobstructed zone defined by the remainder of the cross section of said vessel and which extends from one longitudinal end to the other longitudinal end of said vessel and a multitude of separate horizontally spaced-apart compartments the inner ends of which compartments are open to said unobstructed zone, said compartments otherwise being isolated from each other, whereby a layer of starting species and an electrophoresis or isoelectric focusing medium can be placed in said unobstructed zone and subjected to electrophoresis or isoelectric focusing therein and then fractions of said starting species can be moved into said compartments by turning said vessel about the horizontal longitudinal axis thereof.

2. An apparatus as claimed in claim 1 in which said partitions occupy less than one-half of the cross-sectional area of said vessel.

3. An apparatus as claimed in claim 1 wherein said vessel is an elongated hollow tube which is closed at its ends by said end walls, said tube having a movable side wall portion which can be moved relative to the remainder of said tube for access to the interior of said tube, said electrodes being mounted on said end walls.

4. An apparatus as claimed in claim 3 in which said tube is of substantially circular cross-section.

5. An apparatus as claimed in claim 3 in which said tube is of polygonal cross-section.

6. An apparatus as claimed in claim 3 in which said tube is of hexagonal cross-section, said partitions are flat plates which are horizontally spaced from each other substantially equal distances, said partitions occupying less than one-half of the cross-sectional area of said hexagonal tube and being united to three adjacent side wall portions defining one-half of said tube, another of said side wall portions of the tube defining said movable side wall portion.

7. An apparatus as claimed in claim 6 in which said movable side wall portion is hingedly connected to said hexagonal tube.

* * * * *

UNITED STATES PATENT OFFICE
CERTIFICATE OF CORRECTION

Patent No. 4,234,404          Dated  November 18, 1980

Inventor(s)  Paul S. Satoh

It is certified that error appears in the above-identified patent and that said Letters Patent are hereby corrected as shown below:

Column 2, line  5;  change "manually to ---mutually---.
Column 3, line 32;  change "achieved" to ---received---.
          line 33;  change "functions" to ---fractions---.
          line 51;  "as sucrose" should read
                    ---as a sucrose---.
          line 65;  change "lymphoctyes" to
                    ---lymphocytes---.
Column 4, line 12;  change "in" to ---is---.

Signed and Sealed this

Thirty-first Day of March 1981

[SEAL]

Attest:

RENE D. TEGTMEYER

Attesting Officer      Acting Commissioner of Patents and Trademarks